United States Patent [19]

Stamatakis et al.

[11] Patent Number: 4,615,841

[45] Date of Patent: Oct. 7, 1986

[54] PROCESS FOR MAKING ALKALINE-EARTH METAL SALTS OF ALKARYL SULFONIC ACIDS

[75] Inventors: Emanuel Stamatakis; Thomas E. Sample, Jr.; Paul H. Javora, all of Houston, Tex.

[73] Assignee: Dresser Industries, Inc., Dallas, Tex.

[21] Appl. No.: 727,055

[22] Filed: Apr. 25, 1985

Related U.S. Application Data

[63] Continuation of Ser. No. 534,905, Sep. 22, 1983, abandoned.

[51] Int. Cl.$^4$ ............................................. C07C 143/24
[52] U.S. Cl. .................................. 260/505 N; 252/33; 252/33.3; 44/76
[58] Field of Search ....................... 252/33, 33.3; 44/76, 44/57; 260/505 N

[56] References Cited

U.S. PATENT DOCUMENTS

| | | | |
|---|---|---|---|
| 2,779,784 | 1/1957 | Sharrah | 260/505 N |
| 3,609,076 | 9/1971 | Sabol et al. | 44/57 |
| 3,719,596 | 3/1973 | Shore et al. | 260/505 N |
| 4,206,062 | 6/1980 | Derbyshire et al. | 252/33.3 |
| 4,279,837 | 7/1981 | Wellbrock | 260/505 N |

Primary Examiner—William R. Dixon, Jr.
Assistant Examiner—Margaret B. Medley
Attorney, Agent, or Firm—J. Hughes Powell; Richard M. Byron

[57] ABSTRACT

A novel process for making solutions of alkaline-earth metal salts of alkaryl sulfonic acids that contain about 1.5 to less than three weight percent water and that does not require an azeotropic distillation step to reduce the water of the reaction product to this level, comprises reacting an alkaryl sulfonic acid with alkaline-earth metal oxide in an organic solvent in the presence of 0.05 to less than 2.5 weight percent water. Calcium oxide, alkylbenzene sulfonic acids wherein the alkyl groups contain 10 to 14 carbon atoms, solvent mixtures of lower alkanols and non-polar hydrocarbon solvents all are representative of materials useful in the process of the invention, wherein the alkyl benzene sulfonic acid is preferably proportioned into a mixture of the other reactants and the water is supplied in admixture with a small amount of a calcium alkylbenzene sulfonate.

12 Claims, No Drawings

PROCESS FOR MAKING ALKALINE-EARTH METAL SALTS OF ALKARYL SULFONIC ACIDS

This is a continuation of application Ser. No. 534,905, filed Sept. 22, 1983, now abandoned.

BACKGROUND OF THE INVENTION

Alkaline-earth metal salts of alkylbenzene sulfonic acids find many commercial uses, including use as additives in lubricating oils; as corrosion inhibitors, in antifreeze formulations for example; in rust-proofing compositions, in drilling mud formulations, and the like. As is obvious, these materials find many large volume uses and cost becomes an important factor. Manufacturing methods for preparing such materials are described in many patents. Generally alkylbenzene sulfonic acids are reacted with calcium hydroxide in an aqueous-organic solvent, and thereafter the water and most of the solvents are removed by distillation. Typical are U.S. Pat. Nos. 3,719,596 and 2,799,784.

In U.S. Pat. No. 3,719,596 there is described a method of preparing alkaline-earth alkylbenzene sulfonates. The process comprises forming a suspension of an alkaline-earth metal hydroxide with a water-immiscible azeotrope-forming liquid such as toluene, xylene, tetrachloroethylene or the like, and water, adding thereto a higher alkylbenzene sulfonic acid in a sufficient amount to form the double salt, lowering the pH to an acidic range thereby neutralizing the hydroxide, adding a lower alkanolamine having from 1 to 3 hydroxy groups such as diethylanolamine to neutralize the system and solubilize the salt, and finally, removing practically all of the water by distillation in the presence of a polyhydric alcohol such as ethylene glycol. Monohydric alcohols such as isopropanol are taught to be in appropriate for this use.

There is disclosed in U.S. Pat. No. 2,779,784 a method for making alkaline earth metal sulfonates by heating a mixture of an oil-soluble alkaryl sulfonic acid and an alkaline earth metal compound, preferably in the presence of a solvent, with water at a temperature above 220° F. to 390° F. and under superatmospheric pressure, and removing the water by azeotropic distillation. The alkaline earth metal compound to neutralize the sulfonic acid includes alcholoates, borates, carbonates, carboxylate, hydroxides, hydrates, hydrosulfide, oxides, nitrate, sulfide, thiocarbonates, and others of magnesium, calcium, strontium and barium. The water used is present in amount equal to 5 (50%) to 100 parts per 10 parts of alkaline earth metal compound. The patent teaches that "When an organic sulfonic acid and an alkaline earth metal compound in excess of that required to neutralize the sulfonic acid are agitated together in the presence of an appreciable amount of water at a temperature above 220° F., and under sufficient pressure to hold the water in the liquid state, the water provides a condition whereby the excess alkaline earth metal compound forms a stable dispersion. If the reaction is carried out in an open kettle, the water escapes before the reactants reach the temperature at which dispersion of the alkaline earth metal compound is most suitably obtained."

In U.S. Pat. No. 4,279,837, the alkyl benzene sulfonic acids are neutralized with the necessary amount of basic alkaline earth metal compound in an inert organic solvent in the presence of 1 to 10% by weight of a oxalkylate, and the mixture is then azeotropically distilled to remove the water and a large part of the organic solvent.

A less complex and less costly process for making solutions of alkaline earth metal salts of alkaryl sulfonic acids having a low water content is desired. The elimination of a costly azeotropic distillation step is particularly desirable since this would make possible the elimination of costly equipment, some reagents, waste storage, and disposal, would use less energy, and would result in more efficient use of of existing facilities.

SUMMARY OF THE INVENTION

A novel process for making solutions of alkaline-earth metal salts of alkaryl sulfonic acids that contain about 1.5 to less than four weight percent water and that does not require an azeotropic distillation step to obtain a product containing water at this level, comprises reacting an alkaryl sulfonic acid with alkaline-earth metal oxide and greater than 0.05 to less than about 2.5 weight percent water in an organic solvent.

DETAILED DESCRIPTION

A number of advantages are realized from the novel process of this invention. Eliminating the azeotropic distillation step, that is an essential part of commercial processes also eliminates the need for expenditure of costly energy required for a distillation process, along with the equipment required for azetropic distillation, and the cleaning and maintenance associated with the operation thereof. Also eliminated is the water containing distillate of the distillation step. The water had to be removed from this inert solvent before it could be used again, or if it was discarded, this represents a cost that is saved, also accompanied by the need for fewer storage vessels and other related equipment. Further, the total processing time per batch is reduced by eliminating this step, resulting in more production and lower cost per unit of equipment used. There are many other obvious advantages in the use of the novel process of this invention. The reaction does not need to be heated to reflux because it generates its own heat by reaction; nor is supratmospheric pressure required. While the defined solutions of this invention, containing less than 3 weight percent water, are obtained without requiring an azeotropic distillation step, should one wish to further reduce the water content of the solutions to a lower level, this can be economically done by utilizing the heat generated by the reaction in the process of this invention to distill off the desired amount of water. This represents an improvement over the prior art in that less water is present initially and it is not necessay to add heat to distill off the water, both being an economic advantage.

In the novel process of this invention, the necessary ingredients are a polar organic solvent, an alkaline-earth metal oxide, the defined amounts of water and an alkaryl sulfonic acid.

While any polar organic solvent is contemplated, normally used aree alkanols containing 1 to 8 carbon atoms, such as ethanol, propanol, isopropanol, butanol, isobutanol, pentanol, heptanol, octanol, diols such as ethylene glycol alone or with ethers such as butyl cellosolve, ethylene glycol, monobutylether and the like. Isopropanol and isobutanol are useful alcohols for commercial operations. While the alsohol can be used alone, it has been found that excellent reqults are obtained when the alcohol is mixed with a non-polar solvent, normally a hydrocarbon solvent such as hexane, heptane, mineral spirits, benzene, cyclohexane and the like. Diesel fuel oil ASTM #2 has been found to be satisfactory when mixed with alcohols, including isopropanol or ethylene glycol. The amounts of polar solvents including alsohols used in polar/non-polar solvent mixtures normally will be from about 15 weight percent of the solvent mixture to 100 weight percent alkanol. About one-third or more of alcohol to about one-half are normally used with the non-polar solvent. With diesel oil, a useful ratio is about 60% diesel oil and about 40% isopropanol. The water content of the solvents is preferably below about 0.1 weight percent.

The process of this invention may be used to make alkaline-earth metal salts of a great variety of alkaryl sulfonic acids. The alkyl groups may contain from 3 to 30 carbon atoms, and the aryl groups may be derived from benzene, naphthalene, anthracene, and phenanthrene. More preferably, the alkyl groups contain 8 to 20 carbon atoms. A particularly useul group of alkylbenzene and alkylnaphthalene sulfonic acids have alkyl groups that contain 10 to 14 carbon atoms, such as decylbenzene sulfonic acid, dodecylbenzeene sulfonic acid, tetradecane sulfonic acid, dodecylnaphthyl sulfonic acid and the like.

While the process may be practiced with other alkaline-earth metal oxides as magnesium oxide, strontium oxide, barium oxide and the like, particularly good results are obtained with calcium oxide. A stoichiometric amount of calcium oxide is normally used in relation to the alkaryl sulfonic acid, and a slight excess insures good conversion of the sulfonic acid groups to the salt.

The alkaline-earth metal oxide should be substantially free of lumps and preferably is in a finely divided state. One form that is satissfactory is pulverized so that 98 to 99.5% that will pass a No. 325 mesh sieve. Normally the particle size will range from about 200 to 400 mesh.

The amount of water present in the reaction is critical and control thereof is essential to the practice of the invention. The amount of water used must be such that the final product of the reaction mixture contains less than about 4 i.e. as 3.5 weight percent, preferably less than about 2.5 weight percent water so that no distillation step is required to obtain a product with this water content. The total amount of water present during the course of the reaction preferably should not be greater than about 2 weight percent of the total reactants charged, and less than 25 weiht percent, preferably less than 10 weight percent of the amount of alkaline-earth metal oxide used. Normally the amount of water used in the reaction will be greater than about 0.05 weight percent, preferably greater than about 0.10 weight percent to less than about 2 weight percent. A practical amount of water present in the reactor before the alkaryl sulfonic acid is aded is about 0.15 to about 0.5 weight percent of the total reactants used, preferably about 0.20 to 0.25. The amount of water in the other reactants, if ay, is such that the overall amount of water in the final product normally is less than about 3.5%. Practically the solvents and the alkaryl sulfonic acid should contain less than about 1 weight percent water, normally les than about 0.5 weight percent water, and normally are water free. One convenient method to add the water to the reaction mixture and as an aid in controlling the amount used, is to use as one of the materials in the reaction, at least about 5 to about 10 weight percent or more of a calcium alkaryl sulfonate solution, containing about 40 to 70 weight percent of calcium alkaryl sulfonate and less than about 2.5 weight percent water, added to the reaction mixture before adition of the alkaryl sulfonic acid. These amounts normally will be enough to provide the desired amount of water. The source may be from a commercial preparation of the alkaline-earth metal alkaryl sulfonate. Materials contemplated include solutions prepared by commercial processes. Such materials may contain as much as 4 weight percent or more water, and the amounts of solution used normally will be adjusted to meet the criteria for water present set forth above. Preferably these starter or seed materials contain less than 5 weight percent water, the remainder normally being the solvent used and the alkaryl sulfonate. The total solids o the solution normally vary from about 40 to about ζweight percent, but may be less or more as desired such as about 20 to 80 weight pecent. Solvent-free sulfonates containing the defined amounts of water may be used. Use of these materials provides a particularly useful way to add and control the amount water required and used, and results in an excellent reaction, particularly in the initial stages. Addition of water by this method is unique in that the water required to initiate the reaction does not add to or increase the final weight percent of water based on the total solids in the final product.

Preferably the alkaryl sulfonic acid is proportioned into the reaction mixture at a rate to initiate and sustain the salt forming reaction step, as evidenced by a continued increase in the reaction temperature, usually in commercial equipment to a reflux state of the reaction mixture. While high temperatures and supratmospheric pressure are not required, the reaction can be conducted in closed reactors. The rate to be used is readily determined by those skilled in the art. If the rate of addition is too slow, the reaction slows down, and if the rate of adition is too fast, the reaction will slow down, the temperature decrease, and the reaction may stop.

The pH of the reaction mixture, even after the raction is complete, may be less than 7. Because of potential corosion problems in storage and later use, this is normally adjusted to about 8 or 9 by addiition of a basic material. Amines, such as alkanolamines including diethanolamine, have been found to be useful materials.

The practice of the Invention is demonstrated in the following Examples.

EXAMPLE I 62.8 weight parts of isopropanol, 0.55 weight part of water and 18.30 weight parts of calcium oxide were added to and mixed in a reactor equipped with an agitator and reflux means. A mixture of 210.6 weight parts of dodecylbenzene sulfonic acid and 69.8 weight parts of isopropanol was added to the reactor over a four hour period. The temperature of the reaction mixture at the beginning of the reaction was 23.9° C., and at the end of the four hour addition iof the dodecylbenzene sulfonic acid, the temperature was 49.8° C. The reaction was conducted at atmospheric preessure. Essentially complete conversion of the dodecylbenzene sulfonic acid to the calcium salt was obtained. 2.65 weight parts of diethanolamine was added to raise the pH to 8.0. The water content of the reaction product solution was 2.41 weight percent.

EXAMPLE II 326 pounds of No. 2 diesel oil (ASTM) was charged to a 300 gallon reactor and the agitator turned on. 189 pounds of isopropanol was then charged to the reactor, followed by 114 pounds of a solution containing 68.4 pounds of calcium dodecyl benzene sulfonate, 2.28 pounds of water, and 43.3 pounds of isopropanol from a previous reaction. 74 pounds of calcium oxide was then stirred into the mixture. When this was well mixed, the addition of 798 pounds of dodecylbenzene sulfonic acid was begun at a rate of 7 pounds per minute. This additon was completed in 2 hours. The reaction was conducted at atmospheric pressure. The initial temperature before addition of the dodecylbenzene sulfonic acid was begun was 90° F. and at the end of the addition, the temperature was 190° F. The reaction was allowed to continue for an additional 2 hour period. At the end of this period 34 pounds of diethylanolamine was added to adjust the pH to 8.05. The total solids of the solution was 61.0% and the water content was 2.0%.

EXAMPLE III

To a 3000 gallon reactor there was charged 4,366 pounds of No. 2 diesel oil, 2,563 pounds of isopropanol, 2,535 pounds of a solution from a previous reaction containing 1,521 pounds of calcium dodecylbenzene sulfonate, 50.7 pounds of water and 963 pounds of isopropanol, and 1,050 pounds of calcium oxide, with agitation, and at a temperature of about 95° F. The reactor was closed and cooling water turned on. 10,801 pounds of dodecylbenzene sulfonic acid was added to the reactor at a rate of 7 gallons per minute for the first 20 minutes and then the rate was increased so that the remainder of the dodecylbenzene sulfonic acid, 1,093 gallons, was added over a 22 hour period. The temperature 10 minutes after this addition was begun was 125° F. and the cooling water was turned off. At the end of the addition the temperature was 263° F. and the cooling water was turned back on to lower the temperature to 195° F. The reaction was allowed to continue for 1 hour and a sample taken that had a pH of 3.38. After an additional 40 minutes, 301 pounds of diethanolamine was added to the reactor. The final pH was 8.15, the total solids of the solution was 62.1% and the percent free water was 2.24%. The conversion to calcium dodecyl benzene sulfonate was substantially complete.

EXAMPLE IV

To a reactor equipped with agitating and reflux means, 31.4 weight parts of isopropanol, 31.4 weight parts of a solution containing 18.6 weight parts of calcium dodecylbenzene sulfonate in 12.2 weight parts of isopropanol, and 0.628 weight parts of water was added with stirring. A mixture of 210.6 weight parts of dodecylbenzene sulfonic acid and 100.48 weight parts of isopropanol was added to the reactor over a three hour and 18 minute period. The mixture of reactants, before addition of the dodecylbenzene sulfonic acid was begun, was at room temperature, and at the end of the addition, had risen to 49.3° C. 1.25 weight parts of diethanolamine was added to adjust the pH of the reaction product to 8.5 The conversion was essentially 100%, and the water content of the reaction product was 2.79%.

Alkaline-earth metal alkaryl sulfonate solution prepared in accordance with the improved process of this invention are useful as emulsifiers and have excellent detergent properties. These mateeials are useful and find applications as lubricating oil additives, particularly in low water content lube oils; in corrosion inhibiting compositions; in storage rustproofing compositions; in oil field applications to control corrosion; in oil field drilling mud compositions, and the like, as is well known to those skilled in the art.

We claim:

1. A distillation-free process for making calcium alkaryl sulfonate solutions containing less than about 3.5 weight percent water comprising reacting together calcium oxide with an alkaryl sulfonic acid wherein the alkyl groups contain 8 to 20 carbon atoms in a medium containing an alkanol solvent containing 1 to 8 carbon atoms, water, initially preesent in an amount of about 0.10 to about 0.5 weight percent water and in an amount less than 10 weight percent of the calcium oxide present.

2. A process of claim 1 wherein the alkaryl sulfonic acid is a benzene or naphthanlene derivative wherein the alkyl groups contain 10 to 14 carbon atoms, and the alkanol is isopropanol or isobutanol.

3. A process of claim 2 wherein the alkaryl sulfonic acid is dodecylbenzene sulfonic acid.

4. A process of claim 1 wherein the alkaryl sulfonic acid is proportioned into a mixture of said medium, calcium oxide and water, at a rate to at least sustain the reaction of calcium oxide and the alkaryl sulfonic acid to form the salf thereof.

5. A process of claim 4 wherein the medium comprises the alkanol and a non-polar organic solvent, the alkanol being present in the medium in amount of at least 15 weight percent.

6. A process of claim 5 wherein the non-polar solvent is a hydrocarbon.

7. A process of claim 6 wherein the alkyl benzene sulfonic acid is dodecylbenzene sulfonic acid.

8. A distillation-free process for making calcium alkaryl sulfonate solutions containing less than about 3.5 weight percent water comprising reacting together calcium oxide with an alkaryl sulfonic acid wherein the alkyl groups contain 8 to 20 carbon atoms, in a solvent medium comprising an alakanol containing 1 to 8 carbon atoms, water, initially present in an amount of about 0.10 to about 0.5 weight percent and in an amount less than 10 weight percent of the calcium oxide, wherein the water for the calcium oxide and alkaryl sulfonic acid reaction is supplied by adding a calcium alkaryl sulfonate solution containing less than 5 weight percent water, about 20 to 80 weight percent of calcium alkaryl sulfonate and the remainder being solvent, in an amount of said solution to provide the 0.10 to about 0.5 weight percent of water.

9. A process of claim 8 wherein the alkaryl sulfonic acid is a benzene or naphthalene derivative wherein the alkyl groups contain 10 to 14 carbon atoms, the alkanol is isopropanol or isobutanol and there is at least 5 weight percent of the calcium alkaryl sulfonate solution containing 40 to 70 weight percent calcium alkaryl sulfonate and 0.1 to about 4.0 weight percent water added to the reaction prior to the addition of the alkaryl sulfonic acid that is proportioned into the mixture of the solvent, calcium oxide and calcium alkaryl sulfonate.

10. A process of claim 9 wherein the alkaryl sulfonic acid is dodecylbenezene sulfonic acid.

11. A process of claim 10 wherein the medium contains at least 15 weight percent isopropanol and a non-polar hydrocarbon solvent.

12. A process of claim 11 wherein the hydrocarbon solvent is diesel fuel oil.

* * * * *